United States Patent [19]

Shigematsu et al.

[11] Patent Number: 4,748,695
[45] Date of Patent: Jun. 7, 1988

[54] FACE SHIELD ASSEMBLY

[75] Inventors: Nobuo Shigematsu, Urawa; Yoshiaki Haino, Ohmiya, both of Japan

[73] Assignee: Shigematsu Works Co., Ltd., Tokyo, Japan

[21] Appl. No.: 937,913

[22] Filed: Dec. 4, 1986

[30] Foreign Application Priority Data

May 12, 1986 [JP] Japan .................. 61-70035[U]

[51] Int. Cl.$^4$ .................. A42B 3/00; A61F 9/04
[52] U.S. Cl. .................. 2/424; 2/429
[58] Field of Search .................. 2/6, 9, 10, 424, 427, 2/429, 431, 441, 443

[56] References Cited

U.S. PATENT DOCUMENTS

| | | | |
|---|---|---|---|
| 2,631,286 | 3/1953 | Bowers | 2/10 X |
| 2,965,902 | 12/1960 | Louch | 2/9 |
| 3,858,242 | 1/1975 | Gooding | 2/424 X |
| 4,507,809 | 4/1985 | Stepan | 2/424 |

Primary Examiner—Wm. Carter Reynolds
Attorney, Agent, or Firm—Larson and Taylor

[57] ABSTRACT

A face shield assembly having the upper part of both side peripheral portions or the upper part of both side peripheral portions and the upper peripheral portion in an eyepiece, abutted against the frame. The remaining parts of the eyepiece are fitted in the peripheral portion of a view window of the frame. The right and left side upper corner portions of the eye piece are retained in position by a pair of retaining members and each of the retaining members is held in position by a hand-operated screw and an engagement between an engaging opening and a top-enlarged ridge. At least one anchoring bore formed in the side upper corner portion of the eye piece is fitted with a pin formed on the frame such that the eyepiece can be easily replaced without using any tools.

5 Claims, 2 Drawing Sheets

U.S. Patent   Jun. 7, 1988   Sheet 1 of 2   4,748,695
FIG. 1
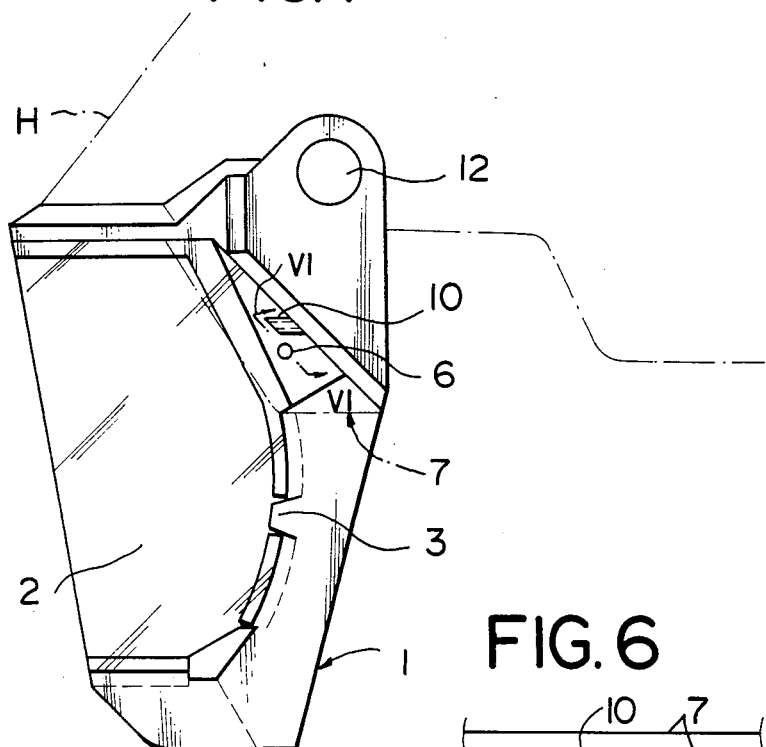
FIG. 6
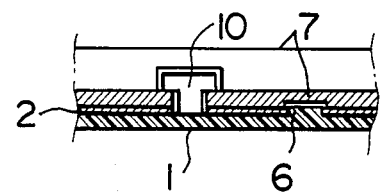
FIG. 3
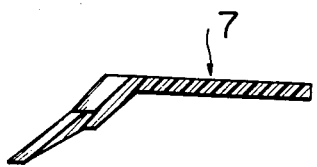
FIG. 4
FIG. 5

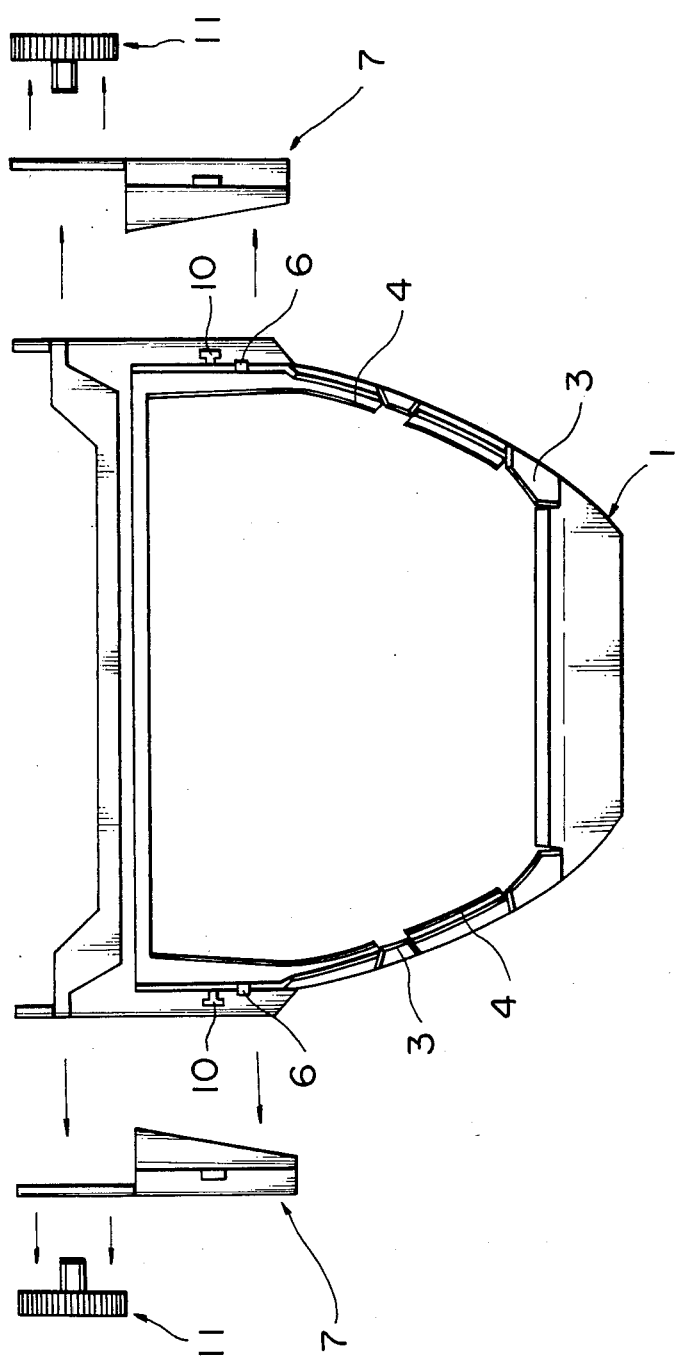

FACE SHIELD ASSEMBLY

FIELD OF THE INVENTION

This invention relates to a face shield assembly which is used to shield a face in welding operation and other work.

DESCRIPTION OF THE PRIOR ART

Generally, an eye-piece of known face shield assemblies is mounted on the frame of a face shield assembly by fixing the peripheral portion of the eye-piece on the frame with screws or by fitting forcedly the entire outer peripheral portion of the eye-piece in between outer and inner holding clicks provided along the inner peripheral portion of the view window of the face shield assembly.

Said known face shield assemblies have disadvantages in that the fixation of eye-piece by means of screws has such a trouble as engaging or disengaging the screws by screw-driver when the eye-piece is mounted and/or replaced while the forced fitting of the entire outer peripheral portion of the eye-piece is involved in a considerable difficulty for the mounting.

SUMMARY OF THE INVENTION

The object of the present invention is to provide an eye-piece mounting structure where an eye-piece can be easily engaged or disengaged without using any tool.

The present invention relates to an eye-piece mounting structure of a face shield assembly in which:

(a) the upper part of both side peripheral portion or the upper part of both side peripheral portion and the upper peripheral portion in an eye-piece are abutted against the outer surface of the face shield frame (1), (b) the remaining parts of the peripheral portion of the eye-piece (2) are fitted in peripheral portion of a view window of the face shield frame, (c) an eye-piece retaining member (7) is abutted against outer surface of both the right and left side upper corner portions of the eye-piece (2) respectively, (d) each of said eye-piece retaining members (7) and (7) is held in its position, by fastening the upper portion of the retaining member with a hand-operated screw (11) with which the face shield is mounted on a helmet (H) or the like, and by engaging an engaging opening or groove (9) formed in the lower portion of the retaining member with at least one head-enlarged pin or the top-enlarged ridge formed on the outer surface of the face shield frame, (e) further, at least one anchoring bore is provided in the eye-piece at the regions where the retaining member is retaining the eye-piece or at the neighborhood of said regions, and each of said anchoring bores is fitted with a pin (6) formed on the outer surface of the face shield frame.

The eye-piece mounting structure of the face shield assembly according to the invention will now be described more in detail, by way of embodiment, with reference to the accompanying drawings in which FIG. 1 is a left side elevation of an embodiment of the face shield assembly according to the invention, in which the eye-piece retaining members (7) are disengaged;

FIG. 2 is a front view of the face shield assembly shown in FIG. 1, where said face shield assembly is disassembled and the eye-piece is removed;

FIG. 3 is a side elevation of the left side eye-piece retaining member;

FIG. 4 is a cross-sectional bottom view taken along the line IV—IV of FIG. 3;

FIG. 5 is a cross-sectional bottom view taken along the line V—V of FIG. 3; and

FIG. 6 is an enlarged fragmentary explanatory view taken along the line VI—VI of FIG. 1, which shows the engaging relationship between the top-enlarged ridge (10) of said frame (1) and the anchoring bore (9) of said retaining member (7).

DETAILED DESCRIPTION OF THE INVENTION

The eye-piece (2) consists of a flexible thin plate such as of a synthetic resin, and both the side peripheral portions and the lower peripheral portion, excepting the upper peripheral portion, of said eye-piece are fitted in between outer and inner clicks (3) and (4) provided in the peripheral portions of the view window of said face shield frame (1). The right and left side upper corner portions of the eye-piece (2) aer retained in their position by means of the retaining members (7) and (7), and the anchoring bores provided in said upper corner portions are fitted with the pins (6) provided on the outer surface of said face shield frame (1). The anchoring bores also extend into the eyepiece. The retaining member (7) is fixed in its position by the engagement of its engaging opening (or groove) (9) with the top-enlarged ridge (10) provided on the frame (1) and by the hand-operated fastening screws (11). The screw may be provided with a groove on its head into which a peripheral portion of a coin can be fitted. Additionally the upper peripheral portion of the eye-piece tightly abuts against the outer surface of the frame (1) by retaining both the right and left upper corner portions of the eye-piece. In the drawings, reference numeral (12) designates a pivotal support opening into which a stud having a threaded bore therein may be rotatably fitted to provide bores for insertion of screws 11.

In such stucture of the face shield assembly of the invention the eye-piece can be disengaged from the frame 1 very easily in such a manner that the screws (11) at both the right and left sides are manually disengaged from their separate threaded bores (not shown) of the helmet the retaining member (7) is moved forwardly so as to be disengaged from the face shield frame (1), then both the upper corner portions of the eye-piece (2) are disengaged from the pins (6), and finally the eye-piece is moved upwardly off the face shield frame. Further, by the reverse operation it is possible to tightly mount the eye-piece on the face shield frame (1) without any difficulty.

In said embodiment the upper peripheral portion of the eye-piece is abutted against the outer surface of the face shield frame (1), but the construction may also be such that the outer and inner clicks are provided even in the upper inner peripheral portion of the frame (1), and the upper peripheral portion of the eye-piece may be fitted in between the outer and the inner clicks.

Depending on use, it will be all right to omit the anchoring bores in both the side upper portions of the eye-piece and the pins (6) which are fitted into said anchoring bores.

What is claimed is:

1. An eye-piece mounting structure of a face shield assembly in which:

(a) the upper part of both side peripheral portions of the eye-piece are abutted against the outer surface of a face shield frame,
(b) the remaining parts of the peripheral portion of the eye-piece are fitted in a peripheral portion of a view window of the face shield,
(c) a pair of eye-piece retaining members are abutted against the outer surface of both the right and left side upper corner portions of the eye-piece respectively,
(d) each of said eye-piece retaining members is held in its position by fastening the upper portion of the retaining member with a hand-operated screw with which the face shield is mounted on a helmet or the like and by engaging an engaging opening or groove formed in the lower portion of the retaining member with at least one head-enlarged pin,
(e) further, at least one anchoring bore is provided at each of both the side upper corner portions of the eye-piece, and each of said anchoring bores is fitted with a pin formed on the outer surface of the face shield frame.

2. An eye-piece mounting structure of a face shield assembly as described in claim 1 wherein the peripheral portion of the view window, in which said remaining parts of the peripheral portion of said eye-piece are fitted, is provided with outer clicks and inner clicks which tightly hold the peripheral portion of the eye-piece.

3. An eye-piece mounting structure of a face shield assembly as claimed in claim 1 wherein the upper peripheral portion in said eye-piece is also abutted against the outer surface of the face shield frame.

4. An eye-piece mounting structure of a face shield assembly in which:
(a) the upper part of both side peripheral portions of the eye-piece are abutted against the outer surface of a face shield frame,
(b) the remaining parts of the peripheral portion of the eye-piece are fitted in a peripheral portion of a view window of the face shield,
(c) a pair of eye-piece retaining members are abutted against the outer surface of both the right and left side upper corner portions of the eye-piece respectively,
(d) each of said eye-piece retaining members is held in its position, by fastening the upper portion of the retaining member with a hand-operated screw with which the retaining member is fixed on the face shield frame, and by engaging an engaging opening or groove formed in the lower portion of the retaining member with at least one head-enlarged pin,
(e) further, at least one anchoring bore is provided at each of both the side upper corner portions of the eye-piece, and each of said anchoring bores is fitted with a pin formed on the outer surface of the face shield frame.

5. An eye-piece mounting structure of a face shield assembly in which:
(a) the upper part of both side peripheral portions of the eye-piece are abutted against the outer surface of a face shield frame,
(b) the remaining parts of the peripheral portion of the eye-piece are fitted in a peripheral portion of a view window of the face shield,
(c) a pair of eye-piece retaining members are abutted against the outer surface of both the right and left side upper corner portions of the eye-piece respectively,
(d) each of said eye-piece retaining members is held in its position by fastening the upper portion of the retaining member with a hand-operated screw with which the face shield is mounted on a helmet or the like and by engaging an engaging opening or groove formed in the lower portion of the retaining member with a top-enlarged ridge formed on the outer surface of the face shield frame,
(e) further, at least one anchoring bore is provided at each of both the side upper corner portions of the eye-piece, and each of said anchoring bores is fitted with a pin formed on the outer surface of the face shield frame.

* * * * *